United States Patent [19]

Grollier

[11] Patent Number: 5,157,036
[45] Date of Patent: Oct. 20, 1992

[54] COMPOSITION FOR INDUCING AND STIMULATING HAIR GROWTH AND RETARDING ITS LOSS, BASED ON NICOTINIC ESTERS AND PYRIMIDINE DERIVATIVES

[75] Inventor: Jean F. Grollier, Paris, France

[73] Assignee: L'Oreal, Paris, France

[21] Appl. No.: 606,154

[22] Filed: Oct. 31, 1990

Related U.S. Application Data

[63] Continuation-in-part of Ser. No. 93,709, Sep. 8, 1987, Pat. No. 4,968,685.

[30] Foreign Application Priority Data

Sep. 8, 1986 [LU] Luxembourg ............................ 86.574

[51] Int. Cl.$^5$ .................... A61K 7/06; A61K 31/505
[52] U.S. Cl. ................................. 514/256; 514/275; 514/356; 514/880; 514/881; 514/944
[58] Field of Search ............... 514/256, 356, 275, 880, 514/881

[56] References Cited

U.S. PATENT DOCUMENTS

| | | | |
|---|---|---|---|
| 2,431,558 | 11/1947 | Huber | 514/356 |
| 3,168,438 | 2/1965 | Halpern | 514/356 |
| 3,461,461 | 8/1969 | Anthony et al. | 544/323 |
| 4,139,619 | 2/1979 | Chidsey, III | 514/275 |
| 4,596,812 | 6/1986 | Chidsey, III et al. | 514/256 |

FOREIGN PATENT DOCUMENTS

| | | | |
|---|---|---|---|
| 47-47663 | 12/1972 | Japan | 514/356 |
| 2096605 | 10/1982 | United Kingdom | 514/356 |

*Primary Examiner*—Dale R. Ore
*Attorney, Agent, or Firm*—Jacobson, Price, Holman & Stern

[57] ABSTRACT

The subject of the invention is a new composition comprising a nicotinic ester with a pyrimidine derivative, to produce hair regrowth much more rapidly than with the pyrimidine derivative alone, the nicotinic ester for its part having no action in respect of hair regrowth. Furthermore, the combination makes it possible to use smaller quantities of pyrimidine derivatives or a lower frequency of application.

14 Claims, No Drawings

COMPOSITION FOR INDUCING AND STIMULATING HAIR GROWTH AND RETARDING ITS LOSS, BASED ON NICOTINIC ESTERS AND PYRIMIDINE DERIVATIVES

This application is a continuation-in-part of application Ser. No. 07/093,709, filed Sep. 8, 1987, now U.S. Pat. No. 4,968,685.

Composition for inducing and stimulating hair growth and retarding its loss, based on nicotinic esters and pyrimidine derivatives.

The invention relates to an active composition for inducing and stimulating hair growth and decreasing its loss, based on nicotinic esters and pyrimidine derivatives.

Man has a stock of 100,000 to 150,000 hairs, and it is normal to lose 50 to 150 hairs daily. The maintenance of this stock results essentially from the fact that the life of a hair is subject to a cycle, known as the pilar cycle, during which the hair forms, grows and falls before being replaced by a new element which appears in the same follicle.

During a pilar cycle, three phases are successively observed, namely, the anagen phase, the catagen phase and the telogen phase.

During the first, so-called anagen phase, the hair undergoes a period of active growth associated with an intensive metabolic activity in the bulb.

The second, so-called catagen phase is transitory and marked by a slowing-down of the mitotic activity. During this phase, the hair undergoes involution, the follicle atrophies and its dermal implantation is seen to be increasingly higher.

The terminal, so-called telogen phase corresponds to a period of rest of the follicle and the hair ends by being shed, pushed by an incipient anagen hair.

This process of continuous physical renewal undergoes a natural change during ageing; the hairs become thinner and their cycles shorter.

Alopecia occurs when this process of physical renewal is accelerated or disturbed, that is to say when the growth phases are shortened, the hairs proceed to the telogen phase earlier and they are shed in larger numbers. The successive growth cycles lead to increasingly thinner and increasingly shorter hairs, converting gradually to an unpigmented down. This phenomenon may lead to baldness.

The pilar cycle is dependent on many factors which are capable of causing more or less pronounced alopecia. Among these factors, dietary, endocrine, nervous, etc., factors may be mentioned. The variation of these different categories of hair is determined by means of a trichogram.

Compositions which enable the effect of alopecia to be eliminated or reduced, and in particular enable hair growth to be induced or stimulated or its loss decreased, have been sought for many years in the cosmetics or pharmaceutical industry.

For this purpose, compounds such as 6-amino-1,2-dihydro-1-hydroxy-2-imino-4-piperidinopyrimidine and its derivatives have already been proposed. Such compounds are described, in particular, in U.S. Pat. No. 4,139,619.

It has also been proposed in patent WO-A-83/02,558 to combine retinoids with the abovementioned compounds.

It is known, moreover, that solutions of nicotinic esters exert a vasodilatory and rubefacient action when applied topically on the skin.

It has been found, however, that vasodilation alone is not sufficient for stimulating hair growth, especially in areas effected by alopecia.

Moreover, the laws which govern the triggering and control of successive pilar cycles are complex, and the mechanism of the stimulation of hair growth is still poorly understood.

The Applicant has now discovered that, by combining a nicotinic ester with a pyrimidine derivative, it was possible to obtain an effect of hair regrowth much more rapidly than with the pyrimidine derivative alone, the nicotinic ester for its part having no action in respect of hair regrowth. Furthermore, the combination makes it possible to use smaller quantities of pyrimidine derivatives with/or a lower frequency of application.

The subject of the invention is hence a new composition for inducing and stimulating hair growth and decreasing its loss, containing, in a cosmetically or pharmaceutically acceptable medium, at least one nicotinic ester and a compound corresponding to the formula:

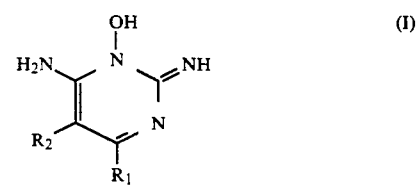

in which $R_1$ denotes a group

in which $R_3$ and $R_4$ can be chosen from hydrogen, an alkyl group preferably having 1 to 4 carbon atoms, and an alkenyl, alkylaryl or lower cycloalkyl group, and $R_3$ and $R_4$ can also form a heterocyclic ring with the nitrogen atom to which they are attached, it being possible for this heterocyclic ring to be chosen, inter alia, from aziridinyl, azetidinyl, pyrrolidinyl, piperidyl, hexahydroazepinyl, heptamethyleneimine, octamethyleneimine, morpholine and 4-(lower alkyl)piperazidinyl groups, it being possible for the heterocyclic groups to be substituted on the carbon atoms with one to three lower alkyl, hydroxyl or alkoxy groups; the group $R_2$ is chosen from hydrogen and an alkyl, alkenyl, alkylalkoxy, cycloalkyl, aryl, alkylaryl, arylalkyl, alkylarylalkyl, alkoxyarylalkyl and lower haloarylalkyl group; as well as the addition salts with cosmetically or pharmaceutically acceptable acids.

The more especially preferred compounds of formula (I) are chosen from the compounds in which $R_2$ denotes hydrogen and $R_1$ denotes a group

in which $R_3$ and $R_4$ form a piperidyl ring.

The especially preferred compound is 6-amino-1,2-dihydro-1-hydroxy-2-imino-4-piperidinopyrimidine.

The nicotinic ester is more especially chosen from $C_1$–$C_6$ linear or branched alkyl, N-alkylaminoalkyl or $C_1$–$C_6$ linear or branched alkylaryl nicotinates, or nicotinates of heterocyclic systems substituted on the carbon atoms with a lower alkyl group and chosen, inter alia, from furfuryl and tetrahydrofurfuryl groups. The preferred compound is methyl nicotinate.

In the definition of compound of formula (I) and of the nicotinic esters, the alkyl and alkoxy groups preferably have from 1 to 4 carbon atoms, the alkylene groups preferably have from 2 to 5 carbon atoms, the cycloalkyl group has preferably 3 to 6 carbon atoms, the aryl group is preferably phenyl.

Further preferred compounds are benzyl nicotinate and tetrahydrofurfuryl nicotinate.

An especially preferred composition according to the invention consists of a composition containing, in a cosmetically or pharmaceutically acceptable medium, at least 6-amino-1,2-dihydro-1-hydroxy-2-imino-4-piperidinopyrimidine and benzyl nicotinate or tetrahydrofurfuryl nicotinate.

The pyrimidine derivative is preferably used in the compositions according to the invention in a proportion of 0.05 to 6% by weight relative to the total weight of the composition, preferably from 0.1 to 5% and more especially from 0.5 to 2% by weight.

The nicotinic ester is preferably used in proportion of between 0.05 and 1% by weight relative to the total weight of the composition, preferably between 0.1 and 0.6% and especially between 0.2 and 0.5% by weight.

The ratio by weight of the pyrimidine derivative to the nicotinic ester is preferably between 2:1 and 10:1.

The cosmetically or pharmaceutically acceptable medium may consist of an alcoholic or hydroalcoholic medium, or alternatively of an emulsion such as a cream, it being possible for these compositions to be pressurized in aerosol.

It is possible to use, in particular, $C_1$–$C_4$ lower alcohols such as ethyl alcohol, isopropyl alcohol and tert-butyl alcohol; alkylene glycols such as propylene glycol and alkyl ethers of mono- and dialkylene glycols, such as ethylene glycol monoethyl ether, propylene glycol monomethyl ether and diethylene glycol monoethyl ether.

The ingredients used in these compositions are ingredients traditionally used in cosmetic or pharmaceutical formulation.

The cosmetically or pharmaceutically acceptable medium may consist of a thickened or gelled aqueous medium or a hydroalcoholic gel, or alternatively an unthickened alcoholic or hydroalcoholic medium.

Agents that are used to thicken or gel these compositions are chosen from heterobiopolysaccharides, cellulose derivatives, crosslinked polyacrylic acids and compounds resulting from the ionic interaction between a cationic polymer, consisting of a copolymer of cellulose grafted with a water-soluble quaternary ammonium monomer salt, or a similarly grafted copolymer of a cellulose derivative, and a carboxylic anionic polymer.

These thickening or gelling agents are preferably used in proportions by weight of 0.1 to 5% by weight relative to the total weight of the composition.

The heterobiopolysaccharides which are useable according to the invention are synthesized by the fermentation of sugars by microorganisms. These heterobiopolysaccharides contain, in particular, mannose, glucose and glucuronic or galacturonic acid units in their chains.

They comprise, more especially, the xanthan gums produced by the bacterium XANTHOMONAS CAMPESTRIS, and the mutants or variants of the latter. The xanthan gums have a molecular weight of between 1,000,000 and 50,000,000.

The xanthan gums contain in their structure three different monosaccharides, namely mannose, glucose and glucuronic acid in salt form.

Among these products, there may be mentioned, more especially, those marketed under the name "KELTROL T" or "TF" by KELCO; "KELZAN S" marketed by KELCO; "RHODOPOL 23 and 23 SC" marketed by RHONE-POULENC; "RHODIGEL 23" sold by RHONE-POULENC; DEUTERON XG marketed by SCHONER GmbH; "ACTIGUM CX9, CS11 and C56" marketed by CECA/SATIA; "KELZAN K9 C 57" marketed by KELCO; "KELZAN K8 B12" marketed by KELCO; and "KELZAN K3 B130", also marketed by KELCO.

The heterobiopolysaccharides may also be chosen from:
a) the biopolymer "PS 87" produced by the bacterium BACILLUS POLYMYXA; this polymer is described in Application EP-A-23,397;
b) the biopolymer "S 88" produced by PSEUDOMONAS strain ATCC 31554; this biopolymer is described in Patent UK-A-2,058,106;
c) the biopolymer "S 130" produced by ALCALIGENES strain ATCC 31555; this polymer is described in Patent UK-A-2,058,107;
d) the biopolymer "S 139" produced by PSEUDOMONAS strain ATCC 31644; this biopolymer is described in U.S. Pat. No. 4,454,316;
e) the biopolymer "S 198" produced by ALCALIGENES strain ATCC 31853; this biopolymer is described in Patent Application EP-A-64,354;
f) the exocellular biopolymer produced by Gram-negative or -positive species of algae, bacteria, yeasts or fungi; this biopolymer is described in Application DE-A-3,224,547.

The cellulose derivatives which are useable according to the invention are represented, more especially, by methylcellulose, hydroxymethylcellulose, carboxymethylcellulose, hydroxybutylcellulose and, more especially, hydroxyethylcellulose, such as the products sold under the name "CELLOSIZE" (QP and WP) by Union Carbide or those sold under the name "NATROSOL" (150, 250) by HERCULES; hydroxypropylcellulose, such as the products sold under the name "KLUCEL" (H, HF, HP, M, EF, G) by HERCULES; methylhydroxyethylcellulose, such as the product sold under the name "TYLOSE MH 300" by HOECHST, and methylhydroxypropylcellulose, such as the product sold under the name "METHOCEL" (E, F, J, K) by DOW CHEMICAL.

The polyacrylic acids are crosslinked with a polyfunctional agent and are chosen, more especially, from the product sold under the name "CARBOPOL" by GOODRICH. In the thickeners resulting from the ionic interaction between a cationic polymer, consisting of a copolymer of cellulose grafted with a water-soluble quaternary ammonium monomer salt, or a similarly grafted copolymer of a cellulose derivative, and a carboxylic anionic polymer, the cationic polymer is preferably chosen from copolymers of hydroxyalkylcellulose grafted by means of a free-radical reaction with a water-soluble quaternary ammonium monomer salt chosen from methacryloylethyltrimethylammonium, methacrylamidopropyltrimethylammonium and dimethyldiallylammonium salts. The carboxylic anionic polymer is preferably chosen from homopolymers of methacrylic acid with a molecular weight, determined by light scattering, of more than 20,000, copolymers of methacrylic acid with a monomer chosen from $C_1$–$C_4$ alkyl acrylates or methacrylates, acrylamide derivatives, maleic acid, a $C_1$–$C_4$ alkyl monomaleate, vinylpyrrolidone and copolymers of ethylene and maleic anhydride. The ratio by weight of the cationic polymer to the carboxylic anionic polymer is between 1:5 and 5:1. Among the products which are more especially preferred, the products chosen are those which result from the ionic interaction of a copolymer of hydroxyethylcellulose grafted by means of a free-radical reaction with diallyldimethylammonium chloride, such as the products sold under the name "CELQUAT L 200" or "H 100" by NATIONAL STARCH, with:

a copolymer of methacrylic acid and methyl methacrylate;

a copolymer of methacrylic acid with ethyl monomaleate;

a copolymer of methacrylic acid with butyl methacrylate;

a copolymer of methacrylic acid with maleic acid.

When the thickened or gelled medium is hydroalcoholic, the thickening or gelling agent is preferably present in proportions by weight of between 0.5 and 5%, and especially between 1 and 3%, relative to the total weight of the composition.

When the thickened or gelled medium is aqueous the thickening or gelling agent is preferably present proportions by weight of between 0.4 and 2%, and more especially between 0.4 and 1.5%, relative to the total weight of the composition.

The activity in respect of hair regrowth could be demonstrated using the known macrophotographic method SAITOH USUKA SAKAMOTO, which consists in cutting the 1 mm from the scalp over a given surface area of order of 0.5 cm$^2$, and then in taking a macrophotograph the area thereby prepared. 1 ml of the composition is applied at the rate of one application per day on an alopecic area of the scalp and the area is photographed again at different successive periods according to this method.

The hairs which do not grow from one photo to the next are those in the telogen phase (T), while those which grow are in the anagen phase (A). The hairs in the T phase and in the A phase are counted and the ratio:

$$\frac{T}{A+T}$$

which characterizes the state of the hair, is determined. T is the number of hairs in the telogen phase, A the number of hairs in the anagen phase.

When this ratio decreases, this corresponds to an improvement in the state of the hair, inasmuch as the latter implies that the hairs in the anagen phase are increasing compared with the hairs in the telogen phase.

The relationship (A+T)/cm$^2$ can also be calculated, and enables the improvement of the hair to be determined from the quantitative standpoint, whereas the former ratio essentially enables the improvement to be defined from the qualitative standpoint, that is to say in terms of the reproduction of the hair. The regrowth effect can also be characterized by the ratio:

$$\frac{A}{T}$$

The process of treatment for inducing and stimulating hair growth or decreasing its loss, which constitutes another subject of the invention, is essentially characterized by the application of the composition as defined above on the alopecic areas of the scalp and on the hair of an individual.

The application may be carried out, for example, after washing the scalp and the hair by means of a shampoo, or shortly after shampooing, this application not being followed by rinsing.

The examples which follow are designed to illustrate the invention without, nevertheless, thereby being limiting in nature.

EXAMPLE 1

The following composition is prepared:

| | |
|---|---|
| 6-Amino-1,2-dihydro-1-hydroxy-2-imino-4-piperidinopyrimidine | 3.0 g |
| Methyl nicotinate | 0.5 g |
| Propylene glycol | 30.0 g |
| Ethyl alcohol | 40.5 g |
| Water | qs 100.0 g |

The activity of the composition for stimulating hair regrowth, compared with a placebo, is assessed by applying 1 ml of this composition at the rate of one application per day, on an alopecic area of the scalp of 5 individuals of average age 40 years.

In the space of two months of treatment, the composition effectively improves the state of the hair.

EXAMPLE 2

A gel is prepared which is active for stimulating hair regrowth, having the following composition:

| | |
|---|---|
| 6-Amino-1,2-dihydro-1-hydroxy-2-imino-4-piperidinopyrimidine | 2.0 g |
| Methyl nicotinate | 0.3 g |
| Propylene glycol monomethyl ether sold under the trade name "DOWANOL PM" by DOW CHEMICAL | 20.0 g |
| Hydroxypropylcellulose sold under the trade name "KLUCEL G" by HERCULES | 3.0 g |
| Ethyl alcohol | 30.0 g |
| Water | qs 100.0 g |

EXAMPLE 3

The following composition is prepared:

| | |
|---|---|
| 6-Amino-1,2-dihydro-1-hydroxy-2-imino-4-piperidinopyrimidine | 1.0 g |
| Methyl nicotinate | 0.2 g |
| Ethyl alcohol | 40.5 g |
| Water | qs 100.0 g |

It is found that, from one month of treatment onwards, the A/T ratio has increased by approximately 30%.

EXAMPLE 4

The following composition is prepared:

| | |
|---|---|
| 6-Amino-1,2-dihydro-1-hydroxy-2-imino-4-piperidinopyrimidine | 0.25 g |
| Methyl nicotinate | 0.125 g |
| Crosslinked polyacrylic acid, MW 3 million, sold under the name "CARBOPOL 934" by GOODRICH | 0.5 g |
| Ethylene glycol monoethyl ether | 30.0 g |
| Water | qs 100.0 g |

EXAMPLE 5

The following composition is prepared:

| | |
|---|---|
| 6-Amino-1,2-dihydro-1-hydroxy-2-imino-4-piperidinopyrimidine | 1.0 g |
| Methyl nicotinate | 0.35 g |
| Propylene glycol | 10.0 g |
| Isopropyl alcohol | qs 100.0 g |

EXAMPLE 6

The following composition is prepared:

| | |
|---|---|
| 6-Amino-1,2-dihydro-1-hydroxy-2-imino-4-piperidinopyrimidine | 0.75 g |
| Methyl nicotinate | 0.20 g |
| Xanthan gum sold under the name "KELTROL T" by KELCO | 1.0 g |
| Ethylene glycol monoethyl ether | 30.0 g |
| Water | qs 100.0 g |

EXAMPLE 7

The following composition is prepared:

| | |
|---|---|
| 6-Amino-1,2-dihydro-1-hydroxy-2-imino-4-piperidinopyrimidine | 0.75 g |
| Butyl nicotinate | 0.20 g |
| Xanthan gum sold under the name "KELTROL T" by KELCO | 1.0 g |
| Ethylene glycol monoethyl ether | 30.0 g |
| Water | qs 100.0 g |

EXAMPLE 8

The following composition is prepared:

| | |
|---|---|
| 6-Amino-1,2-dihydro-1-hydroxy-2-imino-4-piperidinopyrimidine | 0.75 g |
| Hexyl nicotinate | 0.20 g |
| Xanthan gum sold under the name "KELTROL T" by KELCO | 1.0 g |
| Ethylene glycol monoethyl ether | 30.0 g |
| Water | qs 100.0 g |

By replacing the hexyl nicotinate of Example 8 or the butyl nicotinate of Example 7 with an isoamyl, diethyl, aminoethyl, benzyl, furfuryl and tetrahydrofurfuryl nicotinate, a similar activity in combating hair loss is obtained.

EXAMPLE 9

The following composition is prepared:

| | |
|---|---|
| 6-Amino-1,2-dihydro-1-hydroxy-2-imino-4-piperidinopyrimidine | 1.0 g |
| Benzyl nicotinate | 0.125 g |
| Ethyl alcohol | 60 g |
| Water | qs 100.0 g |

EXAMPLE 10

The following composition is prepared:

| | |
|---|---|
| 6-Amino-1,2-dihydro-1-hydroxy-2-imino-4-piperidinopyrimidine | 2.0 g |
| tetrahydrofurfuryl nicotinate | 0.15 g |
| Propylene glycol | 10.0 g |
| Ethanol | qs 100.0 g |

The compositions of examples 9 and 10 have been tested on an organ culture system using mouse vibrissae follicles. An improved effect was noticed for the association, as compared to the effect of Minoxidil alone.

We claim:

1. A composition for inducing and stimulating hair growth and retarding its loss, comprising, in a cosmetically or pharmaceutically acceptable medium, an effective amount of at least one pyrimidine derivative corresponding to the formula:

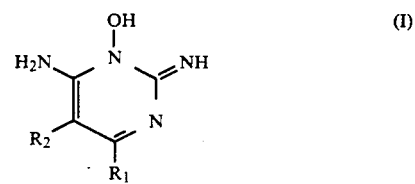

or addition salts of the pyrimidine derivative of formula (I) with cosmetically or pharmaceutically acceptable acids, and an effective amount of at least one $C_1$–$C_6$ linear or branched alkylaryl or tetrahydrofurfuryl nicotinic ester, wherein:

$R_1$ denotes a group

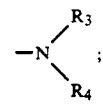

$R_3$ and $R_4$ are selected from the group consisting of hydrogen, $C_1$–$C_4$ alkyl, $C_2$–$C_5$ alkenyl, $C_1$–$C_4$ alkylaryl and lower cycloalkyl group, the alkyl part of which is a $C_1$–$C_4$ alkyl radical, or $R_3$ and $R_4$ together form a heterocyclic ring with the nitrogen atom to which they are attached, this heterocyclic ring being selected from the group consisting of aziridinyl, azetidinyl, pyrrolidinyl, piperidino, hexahydroazepinyl, heptamethyleneimino, octamethyleneimino, morpholino and 4-(lower alkyl)-piperazidinyl, the heterocyclic groups being unsubstituted or substituted on the carbon atoms with one to three $C_1$–$C_4$ alkyl, hydroxyl or $C_1$–$C_4$ alkoxy;

$R_2$ is selected from the group consisting of hydrogen, $C_1$–$C_4$ alkyl, $C_2$–$C_5$ alkenyl, $C_1$–$C_4$ alkoxy, $C_1$–$C_4$ alkyl, cycloalkyl, $C_1$–$C_4$ aryl, $C_1$–$C_4$ alkylaryl, aryl $C_1$-$C_4$ alkyl, $C_1$-$C_4$ alkylaryl $C_1$-$C_4$ alkyl, $C_1$-$C_4$ alkoxyaryl $C_1$-$C_4$ alkyl and haloaryl $C_1$-$C_4$ alkyl;

the concentration of said pyrimidine derivatives or addition salts thereof is between 0.05 and 6% by weight relative to the total weight of the composition;

the concentration of said nicotinic esters is between 0.05 and 1% by weight relative to the total weight of the composition; and said effective amounts are effective for inducing and stimulating hair growth and retarding its loss.

2. The composition of claim 1, wherein said nicotinic ester is benzyl nicotinic ester or tetrahydrofurfuryl nicotinic ester.

3. The composition of claim 1, wherein the pyrimidine derivative of the formula (I) is a compound in which $R_2$ denotes hydrogen and $R_3$ and $R_4$ form a piperidyl ring.

4. The composition of claim 1, wherein the pyrimidine derivative of formula (I) is 6-amino-1,2-dihydro-1-hydroxy-2-imino-4-piperidinopyrimidine.

5. The composition of claim 1, wherein one pyrimidine derivative is 6-amino-1,2-dihydro-1-hydroxy-2-imino-4-piperidinopyrimidine and one nicotinic ester is benzyl nicotinic ester or tetrahydrofurfuryl nicotinic ester.

6. The composition of claim 1, wherein the ratio by weight of the pyrimidine derivative to the nicotinic acid ester is between 2:1 and 10:1.

7. The composition of claim 1, wherein the pharmaceutical or cosmetically acceptable medium is an unthickened hydroalcoholic or alcoholic medium.

8. The composition of claim 1, wherein the cosmetically or pharmaceutically acceptable medium is an aqueous, thickened or gelled medium.

9. The composition of claim 1, which is in the form of a hydroalcoholic gel.

10. The composition of claim 1, wherein the concentration of said pyrimidine derivative or acid addition salt thereof is between 0.1 and 5% by weight relative to the total weight of the composition.

11. The composition of claim 1, wherein the concentration of said nicotinic ester is between 0.1 and 0.6% by weight relative to the total weight of the composition.

12. The composition of claim 1, wherein the alkylaryl nicotinic ester is an alkylphenyl nicotinic ester.

13. The composition of claim 1, wherein the alkyl moiety of the alkylaryl radical of the nicotinic ester is a $C_{1-4}$ linear or branched alkyl moiety.

14. A process for inducing and stimulating hair growth and retarding its loss, comprising applying a sufficient amount of the composition of claim 1 to the hair or scalp of an individual in need of said treatment, wherein said amount is sufficient to induce and stimulate the growth of hair and retard its loss.

* * * * *